United States Patent [19]
Albrecht et al.

[11] Patent Number: 4,931,767
[45] Date of Patent: Jun. 5, 1990

[54] DEVICE FOR VISIBILITY MEASUREMENT FOR A MOTOR VEHICLE

[75] Inventors: Hans Albrecht, Waiblingen; Siegfried Reiniger, Deizsau; Wolfgang Lauer, Esslingen; Hans Spies, Pfaffenhofen; Horst Laucht, Bruckmühl; Martin Spies, Pfaffenhofen, all of Fed. Rep. of Germany

[73] Assignee: Daimler-Benz AG, Stuttgart, Fed. Rep. of Germany

[21] Appl. No.: 258,465

[22] Filed: Oct. 17, 1988

[30] Foreign Application Priority Data

Oct. 17, 1987 [DE] Fed. Rep. of Germany ....... 3735267

[51] Int. Cl.$^5$ ............................................. G01N 21/00
[52] U.S. Cl. ................................. 340/425.5; 340/601; 340/602; 356/342
[58] Field of Search ................. 340/601, 602, 425.5, 340/438, 901, 904, 905; 356/342, 436; 250/574

[56] References Cited

U.S. PATENT DOCUMENTS

| 3,576,557 | 4/1971 | Fruengel | 340/601 |
| 3,782,824 | 1/1974 | Stoliar et al. | 356/342 |
| 4,099,875 | 7/1978 | McMahon et al. | 356/342 |
| 4,502,782 | 3/1985 | Werner et al. | 356/342 X |

FOREIGN PATENT DOCUMENTS

| 0208610 | 1/1987 | European Pat. Off. | 356/342 |
| 2328092 | 12/1973 | Fed. Rep. of Germany. | |
| 2427623 | 12/1975 | Fed. Rep. of Germany. | |
| 0172033 | 8/1986 | Japan | 340/601 |

OTHER PUBLICATIONS

Systems Technology, No. 22, pp. 26–31, Oct. 1975, J. V. Winstanley, "Automatic Fog Warning".

Primary Examiner—Joseph A. Orsino
Assistant Examiner—Brian R. Tumm
Attorney, Agent, or Firm—Evenson, Wands, Edwards, Lenahan & McKeown

[57] ABSTRACT

The device for visibility measurement is designed primarily for use in motor vehicles. A light emitter is arranged inside the driver's compartment preferably on the rear view mirror in front of the windshield. The light emitter generates light pulses or flashes radiating through the windshield. The light scattered back due to soiling on the inside and outside of the windshield or in scatter zones, formed by fog or smoke or the like, in front of the windshield, impinges a light sensor, preferably likewise arranged on the rear view mirror inside the driver's compartment. By utilizing light pulses of various wavelengths and processing of the output signals of the light sensor in predetermined or predeterminable time windows or intervals, not only the respective visibility but also the type of viewing impairment can be determined.

15 Claims, 3 Drawing Sheets

DEVICE FOR VISIBILITY MEASUREMENT FOR A MOTOR VEHICLE

BACKGROUND AND SUMMARY OF THE INVENTION

The invention relates to a device for visibility measurement having a light emitter for generating light pulses, a light sensor for registering the light scattered back from scatter zones, for example particles, in the light path upon emission of the light pulses and an evaluation circuit for converting output signals of the light sensor into control signals of a visibility display or the like.

A corresponding device is the subject of German (published, unexamined patent application [DOS] No. 2,328,092. In that case, light is emitted in a predetermined direction in the form of pulses from a light emitter. Wherever there are scatter zones in the light path, a greater or lesser proportion of the light is reflected onto a light sensor alongside the light emitter. To make it possible that only backscattered light of a scatter zone within a predetermined distance is taken into account, the light sensor is coupled to a gate circuit in order to evaluate only those output signals of the light sensor which occur at the times between predetermined pulses of the light emitter.

In the case of the device known from German (published, unexamined patent application [DOS]), No. 2,427,623, the intensity of the backscattered headlamp light is evaluated on a motor vehicle. For this purpose, a light sensor on the vehicle is arranged, which can only be impinged by light from a narrow angular range in front of the vehicle.

In the case of a modified device described in the DOS No. 2,427,623, two identical light sensors, which are exposed to daylight or ambient light in an identical way, are arranged. One light sensor additionally lies in the light path of a light source. The output signals of the light sensors are evaluated by subtraction. Due to the uniform impingement of both light sensors with ambient light or daylight, here the effect of ambient light or daylight is suppressed, so that only the additional light of the light source is considered. The intensity of the light acting from the light source on the assigned light sensor depends on whether or not there are scatter zones, which may be caused for example by fog or the like, in the light path. In this way, it is avoided that the ambient brightness has an effect on the measurement of visibility.

An object of the invention is now to create an even better adapted device for visibility measurement, for use in motor vehicles.

This object is achieved in the case of a device of the type specified at the beginning by the fact that both the backscatter from scatter zones, such as fog or the like, on the outside of the windscreen or windshield of a driver's compartment or cab of a motor vehicle and the backscatter by soiling, such as deposit or the like, on the windshield can be evaluated by the virtue of the fact that the light emitter and the light sensor are arranged inside the windshield and the light pulses are directed onto the windshield and through it to the outside.

The invention is based on the realization that the soiling of the windshield also has very strong effect on the respective visibility of the driver. Due to the arrangement according to the invention, soiled windshields are automatically taken into account in the measurement of visibility since the light sensor is also impinged if soiling on the windshields leads to backscattering of the light. Furthermore, viewing hindrances in the area outside the windshield are registered, since the light pulses are also directed through the windshield and are accordingly reflected on the outside of the windshield by fog or the like to the light sensor.

According to a preferred embodiment of the invention, the light emitter is arranged such that the light pulses are directed at the zone covered by the windshield wiper of the windshield. Accordingly, the result of the visibility measurement is corrected after actuation of the windshield wipers or of a windshield washing system combined therewith.

A laser diode and a photodiode may expediently be arranged as light emitter and light sensor. Due to the small dimensions of these components, the possibility exists of integrating the same into the rear view mirror of a motor vehicle, arranged on the inside of the windshield.

The device according to the invention can, in principle, operate with visible light. However, in order to avoid any disturbance to the driver, preferred embodiments expediently provide that the light emitter generates light outside the visible wave range, for example infrared light.

It is to be regarded as a particular advantage that, in addition to visibility measurement, the device according to the invention can also be set up for measuring the distance of a fog zone or the like from the vehicle. Consequently, the possibility exists of warning the driver sufficiently long before entering a fog zone or bank.

For this purpose, it is provided that the evaluation circuit processes separately the output signals of the light sensor after emission of a light pulse for a plurality of predeterminable time windows or intervals, the time lapses between the onset of the light pulse and the beginning of the respective time windows or intervals being predeterminable according to various transit times which are required by the light for covering variously long paths which lead from the light emitter to variously remote scatter zones, for example, fog zones, and from there to the light sensor, and that the lengths of time of the light pulse are shorter than the respective transit times.

In the case of this arrangement, account is taken of the fact that the light emitted by the emitter and scattered back to the light sensor at the scatter zones covers variously long light paths depending on the distance of the scatter zone from the light emitter and from the light sensor. So if the light sensor registers the backscattered light intensity at various time lapses after generation of the light Pulse by the light emitter, this is equivalent to the intensities of light scattered back at various distances being registered. So if there is a fog bank some distance away from the visibility measuring device, while the view in the region in front of the fog bank is good, the light sensor will register virtually no light intensity within the time windows or intervals which are assigned to relatively short light paths and thus to scatter zones at a relatively small distance. On the other hand, a comparatively strong light intensity is registered within the time windows or intervals which are assigned to a longer light path and thus to scatter zones in the region of the fog bank. Accordingly, the distance of a fog bank can be established by checking within which time windows or intervals a relative increase in the light intensity at the light sensor occurs.

The evaluation circuit may, as appropriate, have further inputs for the travelling speed of a vehicle or the like and/or weather data.

Consequently, the possibility is created that the evaluation circuit actuates, as a function of the output signals of the light sensor and/or of signals at the further inputs, a display for the visibility, a display for a recommended travelling speed, a speed limitation for the vehicle, a windshield wiper, a windshield washing system and/or a defroster of the windshield.

Other objects, advantages and novel features of the present invention will become apparent from the following detailed description of the invention when considered in conjunction with the accompanying drawings.

DETAILED DESCRIPTION OF HE DRAWINGS

Figure 1:
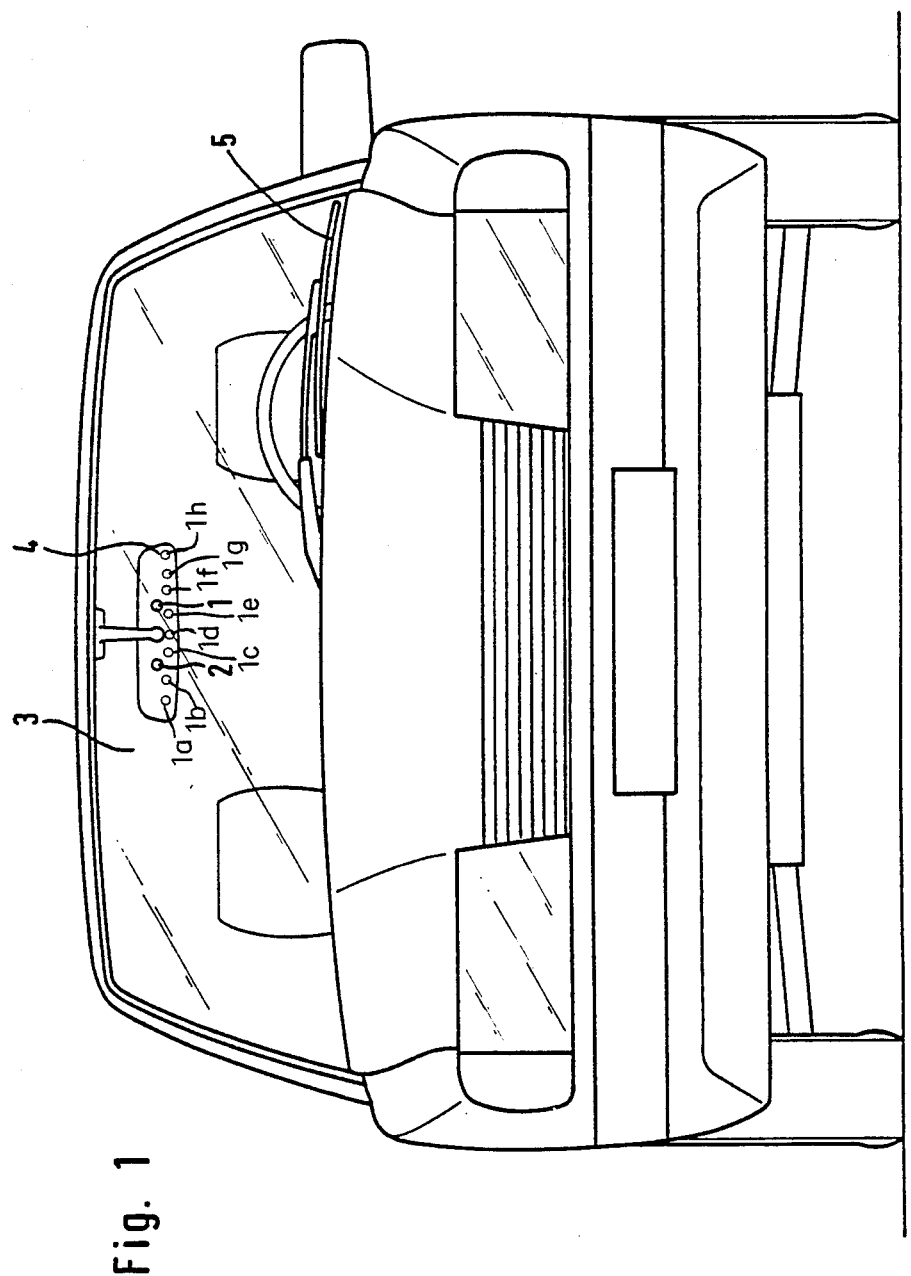
FIG. 1 is a front view of a diagrammatically represented motor vehicle with a device constructed according to the invention for visibility measurement.
Figure 2:
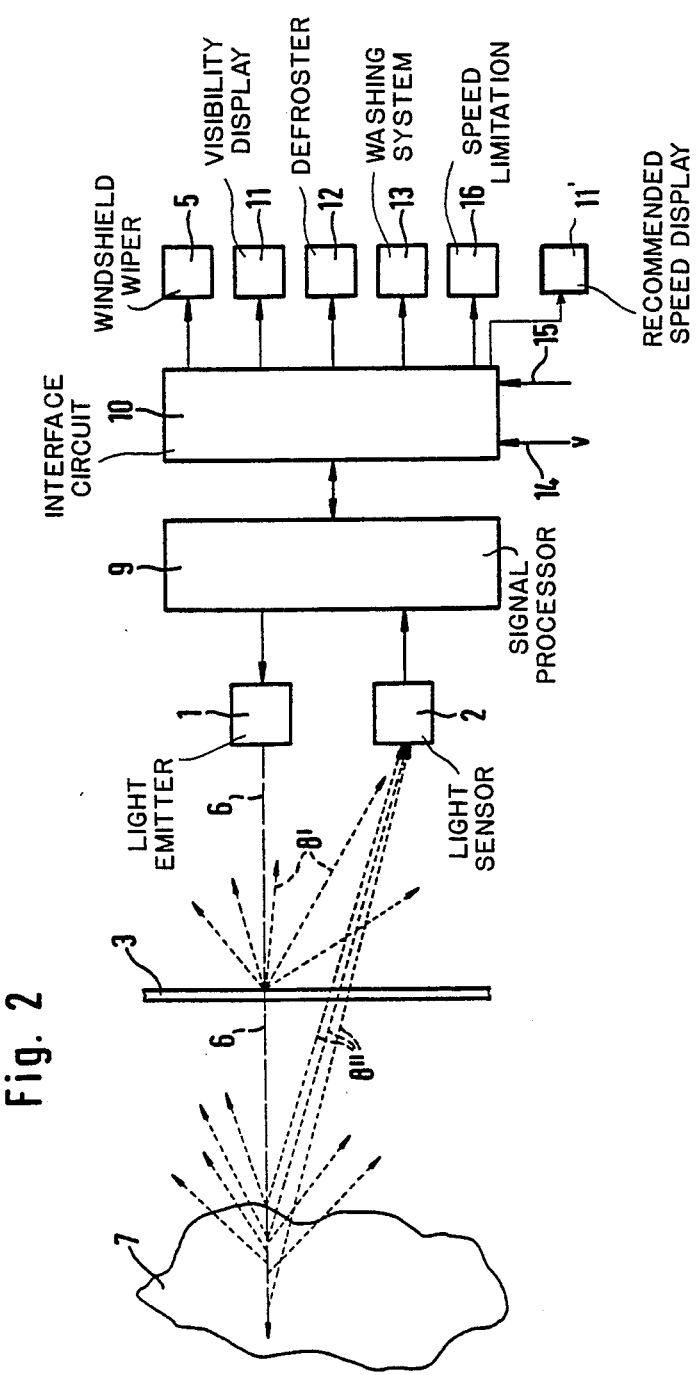
FIG. 2 is a schematic block circuit diagram of the device according to the invention.

According to FIGS. 1 and 2, the device constructed according to the invention for visibility measurement has a light emitter 1, for example a laser diode, or a plurality of light emitters $1a \ldots 1n$ of different wavelengths, and a light sensor 2, for example a photodiode. The light emitter 1 and the light sensor 2 are arranged inside a windshield 3 of a motor vehicle, on a rear view mirror 4. The light emitter 1 generates light flashes which are extremely short in terms of time and the light beams of which are directed approximately in travelling direction of the vehicle at a region of the windshield 3 covered by the windshield wiper 5. Depending on the degree of soiling of the windshield 3, accordingly a greater or lesser proportion of the emitted light is scattered back at the windshield 3. Furthermore, a greater or lesser proportion of the light of the light emitter 1 passing through the windshield 3 is also scattered back if the vehicle passes through an area of fog or approaches a fog bank, or if the visibility conditions are restricted by other airborne substances in the atmosphere, for example smoke or the like.

This is diagrammatically represented in FIG. 2. The light of the light beam 6 emitted by the light emitter 1 is initially scattered back at the windshield 3 and then at a scatter zone 7, formed for example by a fog bank, the backscattered light beams being denoted by 8' and 8", respectively.

The backscattered light beams 8' and 8" fall partly on the light sensor 2, so that the same emits on the output side a signal which reproduces the level of the light intensity intercepted in each case.

In this case, the visibility is all the poorer the greater the intensity of the backscattered light beams 8' and 8".

By means of a signal processor 9, the output signals of the light sensor 2 can be evaluated such that the light beams 8' scattered back from the windshield 3 and the light beams 8" scattered back from the scatter zone 7 can be distinguished.

For this purpose, the light emitter 1 is driven by the signal processor 9 in such a way that the length of time of the light flash generated by the light emitter 1 is, at most, as long as the transit time which is required by the light for covering a path leading along the light beam 6 to the windshield 3 and from there along one of the light beams 8' to the light sensor 2. The duration of time of the light flashes is thus about 1 ns.

Figures 3, 4:
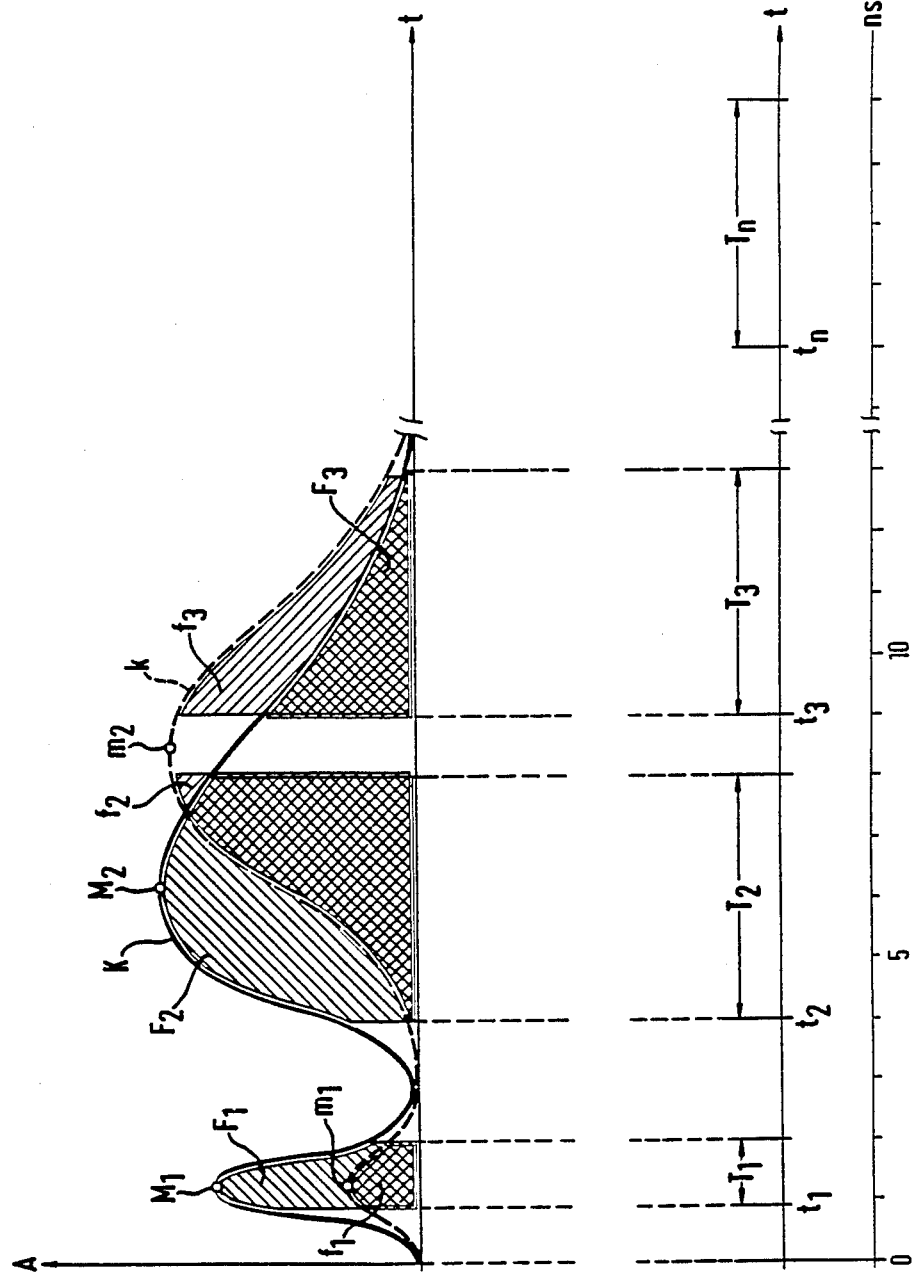
FIG. 3 is an exemplary diagram depicting reproduces the level of the output signals of the light sensor as a function of time of the device of FIGS. 1 and 2.
FIG. 4 the time gates or intervals during which the evaluation circuit processes the output signals of the light sensor reflected in FIG. 3.

On the output side of the light sensor 2, a signal whose amplitude A has, in principle, the progression over time t reproduced by the curve K in FIG. 3, Can then be picked off. The curve K has a first maximum $M_1$, which occurs already after an extremely short time after generation of the light flash by the light emitter 1. This maximum $M_1$ is caused by the partial backscatter of the light beam 6 at the windshield 3.

After a greater time lapse after generation of the light flash by the light emitter 1, a further maximum $M_2$ occurs, when the light beam 6 is scattered back at a scatter zone 7 (cf, FIG. 2) more remote from the windshield of the vehicle. In this case, the position in time of the further maximum $M_2$ is a measure of distance of the scatter zone 7 from the vehicle, since the position in time of the maximum $M_2$ is determined by the transit time of the light from the light emitter 1 to the scatter zone 7 and back to the light sensor 2.

The height and shape of both maxima $M_1$ and $M_2$ is a measure of the viewing impairment which is causd due to the density of the soiling on the windshield 3 and/or of the particle density of the scatter zone 7.

The curve K reproduces as an example the case that the viewing impairment due to soiling of the windshield 3 is relatively strong, accordingly the amplitude A of the output signal of the light sensor 2 at the maximum $M_1$ has a comparatively large value. Otherwise, the relatively small time lapse between the maxima $M_1$ and $M_2$ signifies that the scatter zone 7, for example a fog bank, is a comparatively short distance from the vehicle.

The curve k shows qualitatively the progression over time of the amplitude A for the case that the soiling of the windshield 3 is comparatively small and the scatter zone 7 or fog bank is a greater distance from the vehicle. The maximum $m_1$ accordingly has a small height; in addition, the time lapse of the two Maxima $m_1$ and $m_2$ is relatively large.

The output signals of the light sensor 2 are processed by the signal processor 9, for example by averaging or integration of the amplitudes A. A special feature of the processing here is that the averaging or integration only takes place during predetermined or predeterminable time windows or intervals.

Reference is made in this context to FIG. 4. There, a plurality of time windows or intervals $T_1$, $T_2$, $T_3$ and $T_n$ are plotted on the time axis (t axis). In this case, the time window or interval $T_1$ covers the timed period within which the first maxima $M_1$ or $m_1$ of the amplitude of the light sensor signals according to FIG. 2 are to be expected. The further time window or intervals $T_2$ to $T_n$ cover the time period within which the further maxima $M_2$ or $m_2$ of the amplitude A in FIG. 3 may occur.

The signal processor 9 thus forms for the said time windows or intervals $T_1$ to $T_n$ the time averages or time integrals of the amplitude A. So if the time windows or intervals $T_1$ or $T_n$ begin in each case at the times $t_1$ to $t_n$, the averaging or integration of the amplitudes A is executed successively for the following ranges of values of t:

$$t_1 \leq t \leq t_1 + T_1$$

$$t_2 \leq t \leq t_2 + T_2$$

$$t_3 \leq t \leq t_3 + T_3$$

and $$t_n \leq t \leq t_n + T_n$$

The calculated averages or integrals graphically represent a measure of the area underneath the curves K and k in the range of the values of t given above. These areas are denoted in FIG. 3 in the case of curve K by $F_1$ to $F_3$, in the case of the curve k by $f_1$ to $f_3$. Within the time window or interval $T_n$, the said averages or integrals, or the areas embodying the same, have in the example represented in FIG. 3 virtually the value 0.

The average of integral value calculated for the time window or interval $T_1$ is then a measure of the soiling of the windshield on the inside and outside. The value calculated for the time window or interval $T_2$ is a measure of the viewing hindrance due to fog or the like in a zone affected by the course of airflow in front of the windshield 3. The value calculated for the time window or interval $T_3$ represents a measure of the viewing hindrance due to fog or the like at a distance at which still no disturbance or turbulence due to the vehicle occurs. In the event that the average or the integral of the amplitude A for the time window or interval $T_n$ has a value clearly differing from 0, this means that there is reduced visibility in front of the vehicle. The various time windows or intervals are thus in each case assigned to viewing hindrances at various distances from the light emitter 1 and light sensor 2.

As a departure from the representation in FIG. 4, the time windows or intervals $T_1$ or $T_n$ may also have a shorter length of time and be provided in a greater number. Furthermore, it is also possible to work with time windows or intervals overlapping each other in time.

What is primarily essential is that a processing of the output signals of the light sensor 2, i.e., in the example represented the processing of the signal amplitudes A or the averaging and/or integration, are carried out separately for the individual time windows or intervals $T_1$ to $T_n$.

If appropriate, the values calculated for every two succeeding time windows or intervals may be subtracted from each other. This allows disturbing effects which increase or decrease the values of the amplitude A essentially time-independently by a value which is to the greatest extent constant to be eliminated. By this method of processing, it is expedient that the individual time windows or intervals $T_1$ or $T_n$ have relatively small lengths of time, and succeed each other with close time lapses.

Thus, to summarize, it may be stated that, due to the very short time duration of the light flashes generated by the light emitter 1 and the separate processing of the output signals of the light sensor 2 after time windows and intervals $T_1$ to $T_n$, it is possible to determine both measured values on the degree of viewing hindrance or the degree of visibility and values as to the distance at which a optical scatter zone hindering viewing for example, fog, is located.

In dependence on the date determined for visibility and the distance of optical scatter zones, the signal processor 9 can control, directly or via an interface circuit 10, a display 11 which displays the respective visibility to the driver of the motor vehicle numerically or graphically and a display 11' for displaying a recommended speed. Furthermore, if appropriate, the windshield wiper 5, a defroster 12 or a washing system 13 for the windshield may be actuated automatically in order to clean the same o clear it of deposit.

In particular, if the signal processor 9 or the interface circuit 10 has additional inputs 14 and 15 for the travelling speed v and/or weather data, for example outside temperature and atmospheric humidity, a speed limitation 16 for the vehicle, also taking into account the information available at the inputs 14 and 15, may also be actuated, so that it becomes impossible for the driver to travel at an inappropriately high speed according to the respective visibility or the respective weather conditions.

As a departure from the embodiment represented, light emitter 1 and/or light sensor 2 may also, if appropriate, be arranged in duplicate, the possibility existing with a duplicate arrangement that the two light emitters 1 generate light of different wavelengths. Irrespective of the fact that such a partially or completely redundant arrangement increases the reliability of the device, this may also give rise to the possibility of establishing more accurately the type of viewing hindrance concerned. Optical scatter zones which like fog or smoke consist of a cloud of small particles, namely exhibit a different scattering behavior depending on particle size and wavelength of the light. So if the scattering behavior for light of different wavelengths is evaluated, this may be used to derive information on the particle size, for example it may be possible to distinguish between fog, drizzle and "normal" rain.

Since the laser diodes used with preference as light emitter 1 are able to generate light beams or bundles of extremely small light-up time, any backscattered light there may be is not likely to trouble the driver even if the light generated by the light emitter 1 is in the visible spectral range. Nevertheless, however, it is intended to use light emitters 1 whose spectral range lies outside the spectral range visible to the human eye.

Although the present invention has been described and illustrated in detail, it is to be clearly understood that the same is by way of illustration and example only, and is not to be taken by way of limitation. The spirit and scope of the present invention are to be limited only by the terms of the appended claims.

We claim:

1. Device for visibility measurement for a motor vehicle with a drivers compartment bounded by a windshield, comprising:
    a light emitter means for generating light pulses or flashes,
    a light sensor for registering the light scattered back from scatter zones in the light path upon emission of the light pulses or flashes; and
    an evaluation circuit for converting output signals of the light sensor into control signals for a visibility display,
    wherein both light backscatter from scatter zones outside the windscreen of the driver's compartment and the light backscatter caused by soiling on the windshield can be evaluated by virtue of the fact that the light emitter means and the light sensor are arranged inside the windshield and the light pulses or flashes are directed onto the windshield and through the windshield to the outside; and wherein the light emitter means and the light sensor are arranged on a rear view mirror inside the driver's compartment.

2. Device according to claim 1, wherein the evaluation circuit has further inputs for the travelling speed of a vehicle and/or weather data.

3. Device according to claim 2, wherein the evaluation circuit actuates, as a function of output signals of the light sensor and/or of signals at the further inputs, a display for the visibility, a display for a recommended travelling speed, a speed limitation for the vehicle, a windshield wiper, a windshield washing system and/or a defroster of the windscreen.

4. Device according to claim 1, wherein the light emitter means generate a radiation of light outside the visible wavelength range, in particular infrared light.

5. Device according to claim 1, wherein the light pulses or flashes from the light emitter means are directed at the zone covered by the windshield wiper of the windshield.

6. Device according to claim 1, wherein the evaluation circuit includes means for separately processing the output signals of the light sensor after emission of a light pulse or flash for a plurality of predeterminable time windows or intervals, the time lapses between the onset of the light pulse or flash and the beginning of the respective time windows or intervals being predeterminable according to various transit times which are required by light for covering variously long paths which lead from the light emitter means to variously remote scatter zones and from there to the light sensor, and wherein the duration of the light pulses or flashes are shorter than the respective transmit times.

7. Device according to claim 6, wherein the evaluation circuit forms for each time window or interval a time average or a time integral of the output signals of the light sensor.

8. Device for visibility measurement for a motor vehicle with a driver's compartment bounded by a windshield, comprising:
    a light emitter means for generating light pulses or flashes,
    a light sensor for registering the light scattered back from scatter zones in the light path upon emission of the light pulses or flashes; and
    an evaluation circuit for converting output signals of the light sensor into control signals for a visibility display,
    wherein both light backscatter from scatter zones outside the windscreen of the driver's compartment and the light backscatter caused by soiling on the windshield can be evaluated by virtue of the fact that the light emitter means and the light sensor are arranged inside the windshield and the light pulses or flashes are directed onto the windshield and through the windshield to the outside; and
    wherein said light emitter means includes a plurality of light emitters for light of different wavelengths to facilitate distinction of different types of viewing hindrances.

9. Device according to claim 8, wherein the light emitter means and the light sensor are arranged on a rear view mirror inside the driver's compartment.

10. Device according to claim 9, wherein the light emitter means generate a radiation of light outside the visible wavelength range, in particular infrared light.

11. Device according to claim 10, wherein the light pulses or flashes from the light emitter means are directed at the zone covered by the windshield wiper of the windshield.

12. Device according to claim 11, wherein the evaluation circuit includes means for separately processing the output signals of the light sensor after emission of a light pulse or flash for a plurality of predeterminable time windows or intervals, the time lapses between the onset of the light pulse or flash and the beginning of the respective time windows or intervals being predeterminable according to various transit times which are required by light for covering variously long paths which lead from the light emitter means to variously remote scatter zones and from there to the light sensor, and wherein the duration of the light pulses or flashes are shorter than the respective transit times.

13. Device according to claim 12, wherein the evaluation circuit forms for each time window or interval a time average or a time integral of the output signals of the light sensor.

14. Device according to claim 13, wherein the evaluation circuit has further inputs for the travelling speed of a vehicle and/or weather data.

15. Device according to claim 14, wherein the evaluation circuit actuates, as a function of output signals of the light sensor and/or of signals at the further inputs, a display for the visibility, a display for a recommended travelling speed, a speed limitation for the vehicle, a windscreen wiper, a windscreen washing system and/or a defroster of the windscreen.

* * * * *